US010691828B2

(12) United States Patent
Lehnhardt et al.

(10) Patent No.: US 10,691,828 B2
(45) Date of Patent: Jun. 23, 2020

(54) METHOD FOR SECURING ACCESS TO A RELATION

(71) Applicant: COMPUGROUP MEDICAL SE, Koblenz (DE)

(72) Inventors: Jan Lehnhardt, Koblenz (DE); Tobias Rho, Bonn (DE)

(73) Assignee: COMPUGROUP MEDICAL SE, Kloblenz (DE)

( * ) Notice: Subject to any disclaimer, the term of this patent is extended or adjusted under 35 U.S.C. 154(b) by 163 days.

(21) Appl. No.: 15/855,283

(22) Filed: Dec. 27, 2017

(65) Prior Publication Data
US 2019/0197255 A1    Jun. 27, 2019

(30) Foreign Application Priority Data
Dec. 21, 2017    (EP) ..................... 17209782

(51) Int. Cl.
     *G06F 21/62*      (2013.01)
     *G06F 16/22*      (2019.01)
     (Continued)

(52) U.S. Cl.
     CPC ...... *G06F 21/6245* (2013.01); *G06F 16/2272* (2019.01); *G06F 16/248* (2019.01);
     (Continued)

(58) Field of Classification Search
     CPC ............. G06F 21/6245; G06F 16/9027; G06F 21/6227; G06F 21/602; G06F 16/951;
     (Continued)

(56) References Cited

U.S. PATENT DOCUMENTS

| 2016/0139838 A1* | 5/2016 | D'Sa | G06F 3/0619 711/114 |
| 2017/0039386 A1 | 2/2017 | Lehnhardt et al. | |

(Continued)

FOREIGN PATENT DOCUMENTS

| EP | 2 731 046 A1 | 5/2014 |
| EP | 2731044 A2 | 5/2014 |
| EP | 2731045 A1 | 5/2014 |

OTHER PUBLICATIONS

EESR mailed Jul. 3, 2019, European Application No. EP 18213391.8, 8 pgs.

*Primary Examiner* — Mohammed Waliullah
(74) *Attorney, Agent, or Firm* — J. Clinton Wimbish; Nexsen Pruet, PLLC (57) ABSTRACT

The present disclosure relates to a method for securing access to a first relation. The first relation comprises data items. The data items form a partially ordered set in the first relation. The method comprises: predefining a reference data item; creating a relation and inserting a given data item of the set of data items into the relation; inserting each data item of the set of data items into the created relation using the traversal method, wherein the order comparing step comprises in case a comparison result of the currently traversed data item with the reference data item is different from a comparison result of the to be inserted data item with the reference data item inverting the decision logic, and using the inverted decision logic in the decision step; and providing the created relation.

17 Claims, 6 Drawing Sheets

(51) Int. Cl.
  *G06F 16/28* (2019.01)
  *G06F 16/951* (2019.01)
  *G06F 16/248* (2019.01)
  *G06F 16/901* (2019.01)
  *G06F 21/60* (2013.01)
  *G16H 10/60* (2018.01)

(52) U.S. Cl.
  CPC ........ *G06F 16/284* (2019.01); *G06F 16/9027* (2019.01); *G06F 16/951* (2019.01); *G06F 21/602* (2013.01); *G06F 21/6227* (2013.01); *G16H 10/60* (2018.01)

(58) Field of Classification Search
  CPC .. G06F 16/284; G06F 16/2272; G06F 16/248; G16H 10/60
  See application file for complete search history.

(56) References Cited

U.S. PATENT DOCUMENTS

2017/0041298 A1  2/2017  Lehnhardt et al.
2019/0138642 A1* 5/2019  Pal ..................... G06F 16/2471

* cited by examiner

METHOD FOR SECURING ACCESS TO A RELATION

CROSS REFERENCE TO RELATED APPLICATION(S)

The present application claims priority to European Patent Application No. EP 17 209 782.6, entitled "A METHOD FOR SECURING ACCESS TO A RELATION," filed on Dec. 21, 2017, the entirety of which is herein incorporated by reference.

BACKGROUND

The present disclosure relates to database systems. Specifically, the disclosure relates to a method for building a relation of data items.

Indexes are commonly used to improve the speed of data retrieval operations on a database table at the cost of additional writes and storage space to maintain the index data structure. Indexes are used to quickly locate data without having to search every row in a database table every time a database table is accessed. However, in systems such as medical systems that maintain patient's sensitive data, the indexes may be an additional source of intrusion or of unauthorized access to the health data. Thus, there is a need to ensure a secure access and manipulation of the indexes.

SUMMARY

Various embodiments provide a computer implemented method for building a relation of data items, a computer system, and a computer program product as described by the subject matter of the independent claims. Advantageous embodiments are described in the dependent claims. Embodiments of the present invention can be freely combined with each other if they are not mutually exclusive.

In one aspect, the invention relates to a method for securing access to a first relation, the first relation comprising data items, the data items forming a partially ordered set in the first relation, wherein the insertion of a data item in the first relation is performed by a traversal method for traversing the first relation until reaching an insert position, the traversal method comprising at a currently traversed data item of the first relation: an order comparing step comprising comparing the data item to be inserted with the currently traversed data item resulting in a current comparison result, and a decision step comprising executing a decision logic for selecting one of a first and second sub-relations of the first relation based on the current comparison result in order to perform a next action, wherein the next action comprises a selection of a next data item to be traversed or to identify the insert position in the selected sub-relation, wherein each of the first and second sub-relations comprises zero or more data items succeeding and preceding the currently traversed data item respectively. The method comprises:

predefining (or determining) a reference data item;

creating a second relation and inserting a given data item of the first relation into the second relation;

inserting each data item (other than the given data item) of the first relation into the second relation using the traversal method, wherein the order comparing step comprises in case a comparison result of the currently traversed data item with the reference data item is different from a comparison result of the to be inserted data item with the reference data item inverting the decision logic, and using the inverted decision logic in the decision step;

providing the second relation.

In another aspect, the invention relates to a computer program product comprising computer executable instructions to perform the method as provided in any of the previous embodiments.

In another aspect, the invention relates to a client system comprising a processor and a memory, the memory comprising instructions, wherein the execution of the instructions cause the processor to perform the method.

In another aspect, the invention relates to another method for securing access to a set of data items using relations, a first relation of the relations comprising data items, the data items forming a partially ordered set in the first relation, wherein the insertion of a data item in the first relation is performed by a traversal method for traversing the first relation until reaching an insert position, the traversal method comprising at a currently traversed data item of the first relation: an order comparing step comprising comparing the data item to be inserted with the currently traversed data item resulting in a current comparison result, and a decision step comprising executing a decision logic for selecting one of a first and second sub-relations of the first relation based on the current comparison result in order to perform a next action, wherein the next action comprises a selection of a next data item to be traversed or to identify the insert position in the selected sub-relation, wherein each of the first and second sub-relations comprises zero or more data items succeeding and preceding the currently traversed data item respectively. The method comprises:

predefining a reference data item;

creating a relation and inserting a given data item of the set of data items into the relation;

inserting each data item (other than the given data item) of the set of data items into the created relation using the traversal method, wherein the order comparing step comprises in case a comparison result of the currently traversed data item with the reference data item is different from a comparison result of the to be inserted data item with the reference data item inverting the decision logic, and using the inverted decision logic in the decision step;

in response to receiving a data access request for searching a given data item in the created relation, traversing the created relation comprising: at a currently traversed data item of the created relation: comparing the given data item with the currently traversed data item resulting in a current first comparison result, comparing the given data item with the reference data item resulting in a second comparison result, comparing the currently traversed data item with the reference data item resulting in a third comparison result, based on the first comparison result deciding to select one of a first and second sub-relations of the created relation in order to perform a next action, and in case the second and third comparison results are different inverting the decision by selecting the other one of the first and second sub-relations in order to perform the next action, wherein the next action comprises a selection of a next data item to be traversed and/or to be identified as the data item that satisfies the search request, wherein each of the first and second sub-relations comprises zero or more data items succeeding and preceding the currently traversed data item respectively.

In another aspect, the invention relates to a client system comprising a processor and a memory, the memory comprising instructions that wherein the execution of the instructions cause the processor to perform the other method.

In another aspect, the invention relates to a method for building a relation, wherein the insertion of a data item in an existing relation is performed by a traversal method for traversing the existing relation until reaching an insert position, the traversal method comprising at a currently traversed data item of the existing relation: an order comparing step comprising comparing the data item to be inserted with the currently traversed data item resulting in a current comparison result, and a decision step comprising executing a decision logic for selecting one of a first and second sub-relations of the existing relation based on the current comparison result in order to perform a next action, wherein the next action comprises a selection of a next data item to be traversed or to identify the insert position in the selected sub-relation, wherein each of the first and second sub-relations comprises zero or more data items succeeding and preceding the currently traversed data item respectively. The method comprises:

predefining a reference data item;

upon receiving a data item to be inserted, if the relation is empty inserting the received data item into the relation and if the relation is not empty inserting the received data item into the relation using the traversal method, wherein the order comparing step comprises in case a comparison result of the currently traversed data item with the reference data item is different from a comparison result of the received data item with the reference data item inverting the decision logic, and using the inverted decision logic in the decision step;

providing the relation.

BRIEF DESCRIPTION OF THE SEVERAL VIEWS OF THE DRAWINGS

In the following embodiments of the invention are explained in greater detail, by way of example only, making reference to the drawings in which.

DETAILED DESCRIPTION

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

An example of the relation comprises a tree data structure such as a rooted binary tree and/or a linear set of data items.

A partially ordered set is understood as a set of data elements that formalizes the concept of an ordering, sequencing, or arrangement of the elements of a set. A partially ordered set consists of a set together with a binary relation that indicates that, for certain pairs of elements in the set, one of the elements precedes the other. Such a relation is called a partial order to reflect the fact that not every pair of elements need be related: for some pairs, it may be that neither element precedes in a direct manner the other in the partially ordered set. The partially ordered set may refer to data items of a data structure which are related to each other. The data structure may comprise a tree structure or a similar indexing data structure with pointers or references to the records which contain the corresponding values associated with the data items. For example, the relation may comprise an AVL tree or a binary search tree (BST).

The term "data item" as used herein refers to e.g. a data value of a data element of a set of elements like for example a tuple that comprises one or more data elements, such as a data value of a data field of a data record that has multiple data fields, within a database, such as a relational database, object oriented database, object relational database, hierarchical database, noSQL database, or in-memory database. For example, a medical data record of a patient may comprise various data elements, e.g. data fields, such as name, address, telephone number and medical data fields of that patient where data values for name, address and telephone number are exemplary data items. A data item may comprise a string of characters that may comprise a plurality of letters, numbers, or both. The data item may comprise, in another example, a number having integer value or float value etc. The data items may be configured such that they can be ordered in a predefined order. For example, the data item may comprise a string and may be ordered in accordance with a lexicographical order. For example, expression "string1>string2" indicates that string1 is succeeding string2 following the lexicographical order. And expression "string1<string2" indicates that string1 is preceding string2 following the lexicographical order.

The terms data item and node may be used interchangeably. The data item has a value. For example, a data item being a string may have as value a first name of a patient. And the first name may be referred to as the value of the data item.

The term "user" may refer to an entity e.g., an individual, a computer, or an application executing on a computer that issues requests to insert data items or performing a database search.

For example, the first and second relations are rooted binary trees. The first and second relations may be indexes for accessing second data items e.g. of the first relation any second relations may comprise patient names in the encrypted format and references (or referential connections) to second data items related to that patient in a database. The insertion of data items in the first relation using the traversal method may result in that the lowest ordered data item is the leftmost node of a tree representation of the first relation while the highest ordered data item is the rightmost node in a tree representation of the first relation. This exposes the data's inherent linear order which may contravene and render intuitive the content of the first relation. This may render more guessable the content of the first relation and thus vulnerable against static attacks. In a static attack, an attacker can acquire a copy of the first relation. Having more hints or inputs regarding the structure or content of the first relation may render the access to the content easier. For example, exploiting linear order edges, e.g. items at the leftmost node in the tree representation likely to begin with a character "A" (and vice versa) e.g. the name "Aaron" likely to be leftmost node, and "ZZ" is the rightmost. This may render the content of the first relation guessable.

The present method may enable a secure access to data by making the leftmost and rightmost nodes un-guessable and thus may overcome the above problem.

The reference data item belongs to the same domain or having the same type of the data items to be inserted in the second relation. For example, if the data items to be inserted in the second relation are of string type, the reference data item is a string. For example, the reference data item may be received as input from a user. In another example, the reference data item may be generated randomly such that it contains a predefined number of characters e.g. 3 characters.

The reference data item may for example be determined such that the root node of the first relation and one of the two child nodes of the root node becomes the leftmost and the rightmost nodes of the second relation. This may be done by generating a reference data item that has an order between the root node and that one of the child nodes e.g. if the root node has data item "A" and the child node has data item "C", the referenced data item may be chosen as "B", A<B<C. This may enable a systematic and controlled creation of the second relation while having the advantage of the present method as described herein.

According to one embodiment, the reference data item is a randomly chosen data item that is not part of the first relation. This may further increase the secure aspect of the present invention because the reference data item is chosen independent of the content of the first relation. Having such dependency may compromise the secure access to the first relation.

According to one embodiment, the first relation is stored on a server. The server is coupled to a client computer via a network. The client computer stores the reference data item, wherein the second relation is stored on the server. This may further increase the secure aspect of the present invention as the reference data item is kept separate from the data that has been created using the reference data item e.g. an attacker may not have all elements or building blocks under hand for reading the second relation.

For example, the client computer is a portable electronic telecommunication device, such as a mobile radio or digital cellular mobile telephone, such as a smartphone or tablet computer that have a telecommunication interface, such as a GSM, UMTS, WLAN or other network interface. The servers may, as usual, be located in a third party's location where they are managed e.g. together with other servers. For example, the server may be located outside an access protected enclosed trusted environment. The trusted environment may be a medical practice or another enclosed area in a building, with restricted access. For example the access into the trusted environment can be restricted by means of an electronic access control system and/or physical and/or organizational measures. In the field of the provision of healthcare services this may particularly be beneficial as it enables the use of a mobile portable battery powered client device within the trusted environment in the context of emergency medical services and/or home visits of patients by medical doctors.

According to one embodiment, the first relation constitutes a rooted tree, wherein the given data item is the root node of the first relation, wherein the inserting of each data item of the first relation comprises traversing the first relation and inserting data items of each level of the first relation before moving to the next level of the first relation. This may enable a systematic and efficient access to the first relation for generating the second relation.

According to one embodiment, the first relation is stored on a server. The server is coupled to a client computer via a network, wherein the inserting of a data item of the first relation in the second relation is comprising: requesting by the client computer the data item to be inserted from the server and receiving the requested data item, performing by the client the traversal method, the client further instructing the server for performing the inserting steps.

This may enable traversing the first relation via the server by storing the first relation on the server and executing the traversal method at the client computer, wherein in case the client computer determines which data item of the first relation is to be traversed the client computer requests it from the server and the server responds with the requested data item. In addition, the client computer indicates the position in which a data item is to be inserted in the second relation and may thus send the data item to be inserted and an indication of the position in the second relation such that the server can store the sent data item in the second relation at the position. This may enable a centralized approach for managing relations that may for example be spread over multiple servers and databases.

According to one embodiment, the data items of the first relation are encrypted data items, wherein the receiving of the requested data item comprises decrypting the requested data item. The partial order of the first relation is formed with respect to the data items in non-encrypted form. For example, the data items are stored encrypted with a cryptographic key, wherein the data items form the partially ordered set, the partial order being formed with respect to the data items in non-encrypted form. A "cryptographic key" as used herein encompasses a symmetric key that serves both for encryption and decryption as well as an asymmetric cryptographic key pair.

The retrieval of the data items from the server can be performed without any knowledge of the respective cryptographic key by the server. At no time, the server has to be aware of the cryptographic key or the plain text content of the received data items. Thus, there is no risk of compromising the data items at the database. Nevertheless, standard database techniques can be used for querying the database including usage of indexes. Therefore, the search and retrieval of data items is quick. Further, the amount of data to be transmitted between the client computer and the server is limited to a minimum. For example, only standard queries and retrieved data items may be transmitted between the client computer and the database. This may predestine the employment of the described computer system in a cloud computing environment with the database being part of the cloud. Further, any communication between the client computer and the database is secure since it is encrypted by the first cryptographic key.

According to one embodiment, the inserting of the data item comprises re-encrypting the received data item and sending the encrypted data item to the server in order to be inserted in accordance with the determined next action. This may further secure access to both the first and second relations.

According to one embodiment, the second relation comprises a rooted binary tree, wherein after each inserting step the method comprises rebalancing the second relation in response to determining that the resulting second relation from the inserting step is imbalanced or non-balanced. Searching into a balanced relation may significantly be faster than searching into a non-balanced relation since the levels of the balanced relation are minimized compared to the non-balanced relation.

According to one embodiment, the partially ordered set comprises data items forming a rooted binary tree, wherein the insert position is a leaf node. The second relation is the rooted binary tree.

According to one embodiment, the first relation is an AVL tree. This embodiment may be seamlessly integrated with existing systems such that existing systems benefit from the advantage of the present method.

According to one embodiment, the method further comprises receiving a request for performing one of an equality search, inequality search, interval search and prefix search on the second relation, wherein the execution of the request comprises identifying one or more given data items of the second relation that satisfies the request, wherein identifying a given data item in the second relation that satisfies the received request comprises traversing the second relation comprising: at a currently traversed data item of the second relation: comparing the given data item with the currently traversed data item resulting in a current first comparison result, comparing the given data item with the reference data item resulting in a second comparison result, comparing the currently traversed data item with the reference data item resulting in a third comparison result, based on the first comparison result deciding to select one of a first and second sub-relations of the second relation in order to perform a next action, and in case the second and third comparison results are different inverting the decision by selecting the other one of the first and second sub-relations in order to perform the next action, wherein the next action comprises a selection of a next data item to be traversed and/or to provide the currently traversed data item as the data item that satisfies the request, wherein each of the first and second sub-relations comprises one or more data items succeeding and preceding the currently traversed data item respectively. In one example, for searching further data items that satisfy the request, the second relation may be traversed from the root node and the method described above may be repeated for identifying a further data item that satisfies the request.

For example, the first relation may be associated with a linear data structure: the first data items are annotated with elements of a linear order in the first relation, the linear order corresponding the order in which the first data items are stored in the first relation with respect to the partial ordered set. The linear data structure comprises numbers sortNumber that indicate the position of each data item in the first relation according to the partial order. In case of encrypted first data items, the encrypted first data items are annotated with elements of a linear order in the first relation, the linear order corresponding the order in which the encrypted first data items are stored in the first relation with respect to the partial ordered set.

Generally, interval and prefix searches on the first relation may be evaluated using SELECT statements on the first relation (referred to "table1") such as statement "SELECT*FROM table1 WHERE sortNumber between x AND y", which searches for data items having the sortNumber between x and y, where x and y are the elements of the linear order that correspond to the search boundaries of the interval or prefix search. The search boundaries may for example be obtained by traversing the first relation and identifying the two data items that correspond to the boundaries, wherein x and y are the sortNumber of the identified data items.

The same interval and prefix searches may be performed on the second relation (table2), as described above in order to obtain the elements of the linear order that correspond to the interval boundaries x and y. Then, using the same linear data structure of the first relation, the second relation may be queried with a modified SELECT statement as follows.
if x≤y: SELECT*FROM table2 WHERE sortNumber between x AND y if x>y: SELECT*FROM table2 WHERE sortNumber≥x OR sortNumber≤y. The amended statements take into consideration the new structure of data items in the second relation.

According to one embodiment, the method further comprises replacing the first relation with the second relation in the server and/or redirecting data access request of the first relation to the second relation. This may enable the secure access to the relations. Keeping the first relation in association with the second relation may provide multiple data access options that the user may decide to use based on circumstances.

According to one embodiment, the method further comprises: determining two other reference data items, and for each sub-relation of two sub-relations of the second relation comprising data items succeeding and preceding the given data item respectively, repeating the inserting steps using the sub-relation as the first relation. This may further increase the secure aspect of the present method as it renders the content of the second relation less and less intuitive.

An approach that is suitable especially for data items that are to be stored encrypted in a relation of a database, is that for storage of an encrypted desired data item, the client is traversing, starting from an initial data item of the data items at the database, the existing relation by repeatedly requesting by the client current data items from the database in order with respect to the partial order until the position of the desired data item or the desired data item itself is identified in the partially ordered set. Upon reception of a requested current data item, said data item is decrypted by the client in order to determine which next encrypted current data item to request from the database (left/right node regarding the current data item). Such methods for accessing encrypted data items using a partially ordered set have been disclosed in published European patent applications EP 2 731 044 A2, EP 2 731 045 A1. The contents of the identified publications EP 2 731 044 A2, EP 2 731 045 A1 are hereby incorporated by reference.

In accordance with an embodiment of the invention the data items are tuples or attribute values of an attribute. The above-described procedure can thus be applied either for tuples as a whole, or parts of tuples or to individual attribute values. It has to be noted here, that the description is not limited to single values of an attribute. An attribute may also comprise multiple elements like for example multiple numbers separated from each other by for example, commas, semicolons or even multiple Boolean operators.

Figure 1:
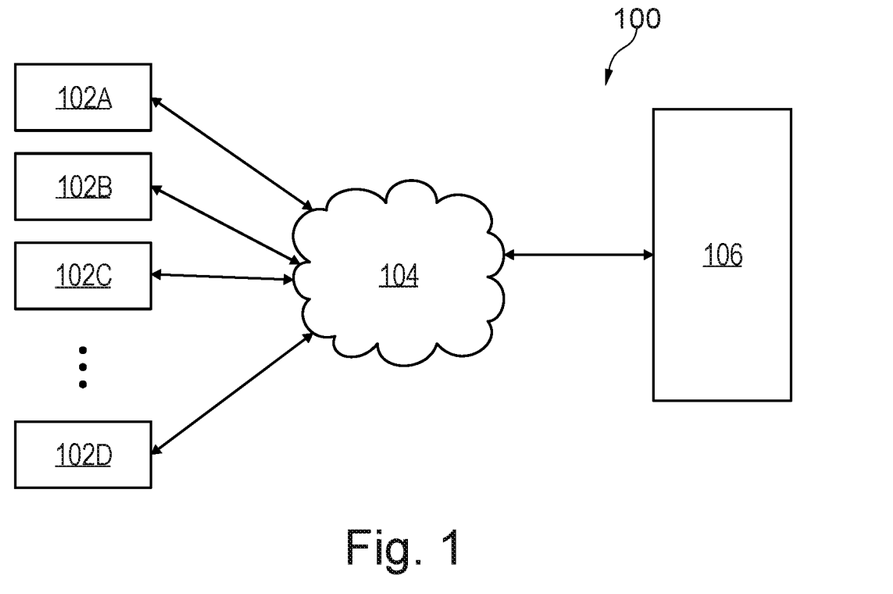
FIG. 1 depicts a schematic block diagram of a client-server system.

FIG. 1 shows a schematic block diagram of a client-server system 100 in accordance with the present disclosure. The client-server system 100 comprises one or more client systems (or client computers) 102A-N and a server system (or server computer) 106. The client system 102A-N and the server system 106 are connected over a network connection 104. The client system 102 can be regarded as a computer system that is able to communicate with the server system 106 via the network connection 104 which comprises for example a wireless local area network (WLAN) connection, WAN (Wide Area Network) connection, LAN (Local Area Network) connection or a combination thereof. The server system 106 can be regarded as a computer system that is able to provide data access to the client system 102. In order to access data stored on the server system 106, the client system 102 sends a request to the server system 106, where the request is received and processed at the server system 106.

For example, client-server system 100 may be a medical system, in which the client system 102A-N may be part of a medical office or a hospital and the server system 106 may be located in an external database center, like a cloud computing center.

For example, a client system 102A-N may comprise a portable electronic telecommunication device, such as a mobile radio, digital cellular mobile telephone, such as a smartphone or tablet computer, palmtop, laptop, notebook, PDA (personal digital assistant), or other mobile computer device which is connectable to network 104. This may particularly be beneficial for applications that involve terrestrial users in vehicles or on foot, such as for emergency responder organizations or public works organizations. In the field of the provision of healthcare services this may particularly be beneficial as it may enable the use of a mobile portable battery powered client device in the context of emergency medical services and/or home visits of patients by medical doctors, while maintaining high data privacy standards.

For example, the client-server system 100 may provide a cloud environment where the multiple client systems 102A-C may form a group of computers that is part of multiple groups or clusters of computers in the cloud environment. The multiple client systems 102A-C may act like a single system that provides services to respective users of the cloud environment. For example, the multiple client systems 102A-C may be assigned a common group public key and a group private key that can be used to (uniformly) encrypt the data at the multiple client systems 102A-C.

For example, the multiple client systems 102A-C may belong to an organizational entity, such as a health service provider, and may be located in a respective access restricted environment, such as a hospital. Access restriction to the environment can be implemented by physical, such as edificial, and/or organizational measures and/or by an electronic access control system. Such restricted environment is a trusted environment in which confidentiality of data items, such as patients' medical records, is preserved.

As used herein the term "server" or server system refers to any computerized component (e.g. a software component), system or entity regardless of form that is adapted to provide data, files, applications, content, or other services to one or more other devices or entities.

The server system 106 is configured for accessing and controlling access to a patient database comprising patient data. The access to the patient database may be performed using a tree data structure.

Figure 2:
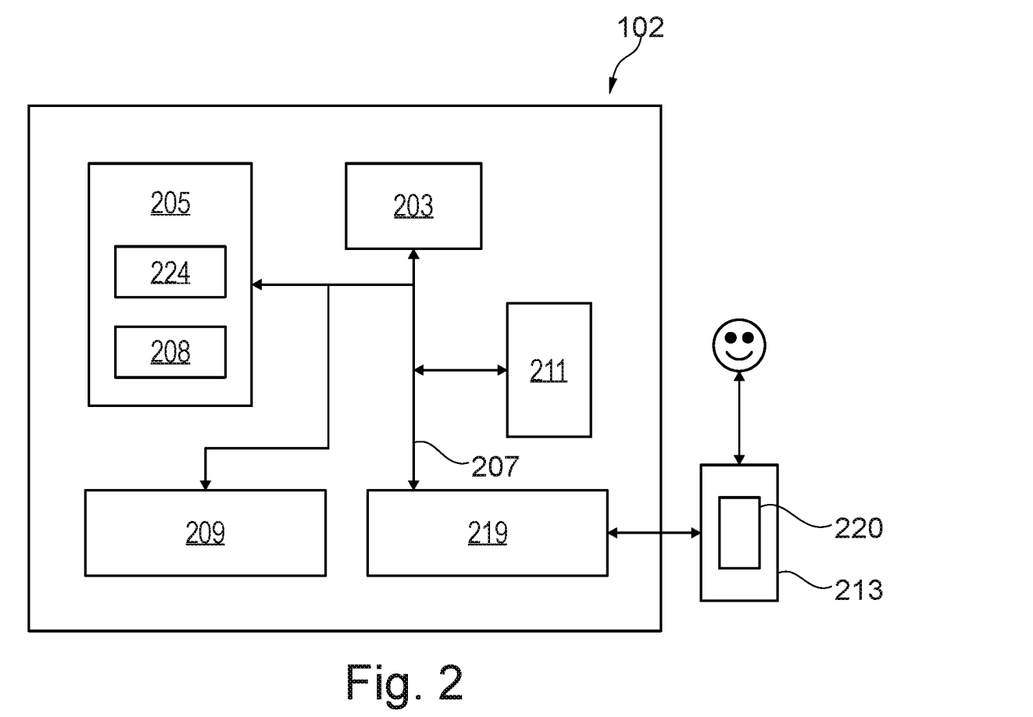
FIG. 2 depicts a schematic block diagram of a client or server system.

FIG. 2 shows a schematic block diagram of a computer system 102 such as one of the client systems 102A-N in accordance with the present disclosure. The components of the computer system 102 may include, but are not limited to, one or more processors or processing units 203, a storage system 211, a memory unit 205, and a bus 207 that couples various system components including memory unit 205 to processor 203. The storage system 211 may include for example a hard disk drive (HDD). The memory unit 205 may include computer system readable media in the form of volatile memory, such as random access memory (RAM) and/or cache memory. The client system 102 typically includes a variety of computer system readable media. Such media may be any available media that is accessible by the client system 102, and it includes both volatile and non-volatile media, removable and non-removable media.

The client system 102 may also communicate with one or more external devices such as a keyboard, a pointing device, a display 213, etc.; one or more devices that enable a user to interact with client system 102; and/or any devices (e.g., network card, modem, etc.) that enable the client system 102 to communicate with one or more other computing devices. Such communication can occur via I/O interface(s) 219. Still yet, the client system 102 can communicate with one or more networks such as a local area network (LAN), a general wide area network (WAN), and/or a public network (e.g., the Internet) via a network adapter 209. As depicted, the network adapter 209 communicates with the other components of the client system 102 via bus 207.

The memory unit 205 is configured to store applications that are executable on the processor 203. For example, the memory unit 205 may comprise an operating system as well as application programs. The application programs comprise a data access application 208. The data access application 208 comprises instructions that when executed enable a user of the client system 102 to request data residing on server system 106 and/or to perform at least part of the present method. For example, the execution of the instructions may cause the processor 203 to display information on a graphical user interface 220. The graphical user interface 220 comprises search fields that are configured to receive inputs indicative for example of data items.

The memory unit 205 may for example store a traversal algorithm or traversal method 224. The traversal algorithm 224 may enable to traverse a rooted tree and insert data items in the rooted tree. The rooted tree may for example be an AVL tree.

The traversal algorithm 224 may be used to traverse the rooted tree until reaching an insert position where to insert a data item. The traversal algorithm 224 comprises at a currently traversed data item of the rooted tree: an order comparing step comprising comparing the data item to be inserted with the currently traversed data item resulting in a current comparison result, and a decision step comprising executing a decision logic for selecting one of a first and second sub-trees of the rooted tree based on the current comparison result in order to perform a next action. The next action comprises a selection of a next data item to be traversed or to identify the insert position in the selected sub-tree. Each of the first and second sub-trees comprises zero or more data items succeeding and preceding the currently traversed data item respectively. In case the traversal method 224 is used for traversing the rooted tree in order to search for a given data item in the rooted tree, and if the current comparison result satisfies the request the next action comprises using the currently traversed data item as the result of the search and optionally (if more than one result data item is required) a selection of a next data item to be traversed in the selected sub-tree. If the current comparison result does not satisfy the request, the next action comprises a selection of a next data item to be traversed in the selected sub-tree.

EP published applications EP 2 731 044 A2, EP 2 731 045 A1 and EP2 731 046 A1 provide further details of the traversal method used for inserting or for querying a relation such as rooted tree. The contents of the identified publications EP 2 731 044 A2, EP 2 731 045 A1 and EP2 731 046 A1 are hereby incorporated by reference.

Figure 3:
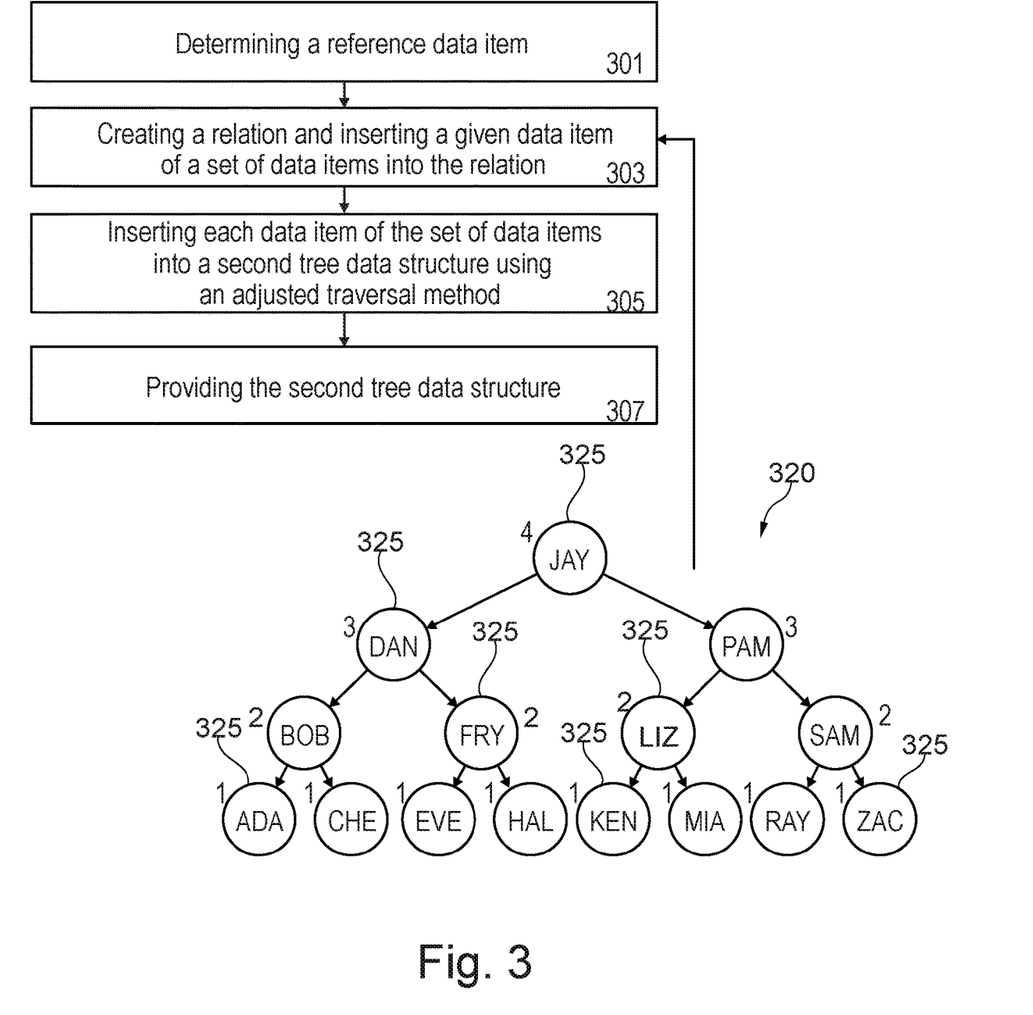
FIG. 3 is a flowchart of a method for securing access to a set of data items.

FIG. 3 is a flowchart of a method for securing access to a set of data items. The set of data items are input for the present method.

The set of data items 325 may or may not be part of an existing relation such as tree data structure 320. For example, the set of data items may be received item by item and may be inserted in the created relation as described herein using an adjusted traversal method.

FIG. 3 further shows the tree data structure 320 having a predefined number of nodes (collectively referred to by 325). Each node 325 of the tree data structure 320 may represent or contain a respective data item. For simplicity of the description the terms "node" and "data item" may be interchangeably used. The tree data structure 320 may be a rooted binary tree.

In this example of FIG. 3, the tree data structure 320 may be the source of the set of data items 325 that are to be used as input for the present method. The set of data items 325 are all data items inserted in the tree data structure 320.

In step 301, a reference data item may be predefined or determined. The reference data item may be referred to as a cyclic shift value. The reference data item may be a randomly chosen data item that is part or not part of the tree data structure 320. For example, the reference data item may be of the same type as the data items 325. As the data items 325 of the tree data structure 320 are strings of characters, the reference data item is a string of character a well. This may enable to compare the reference data item with the data items 320 in accordance with the lexicographical order.

In step 303, a relation may be created and a given data item of the set of data items may be inserted into the relation. The relation created may have a structure as the tree data structure 320. For example, the created relation may be a second tree data structure being a rooted binary tree.

The given data item to be first inserted in the second data structure may be any one of the set of data items 325. Preferably, the given data item may be the root node of the tree data structure 320. The choice of the root node as the first node to be inserted may save processor resources that would otherwise be required for finding another item of the first relation.

In step 305, each data item of the set of data items 325 (excluding the given data item that has been already inserted) may be inserted into the second tree data structure using an adjusted traversal method such that the access to the second tree data structure may be not intuitive and thus more secure.

The adjusted traversal method may be obtained by adjusting the traversal method 224. The traversal method 224 may be adjusted as follows.

As described above, the traversal method comprises the comparing step and the decision step that are executed for each currently traversed data item. The adjusting is performed such that the order comparing step further comprises two other comparisons involving the comparison of the currently traversed data item with the reference data and the comparison of the to be inserted data item with the reference data. The results of the two comparisons are compared and if they are different the decision logic is to be inverted. The inverted logic would then be used in the decision step. This results in the adjusted traversal method which include the additional comparisons and the modified decision logic based on the result of comparison. However, if the results of the two comparisons are not different the decision logic is maintained as it is with the traversal method 224.

For example, assuming that the current content of the second tree data structure comprises three data items A, B and D, where B is the root node, A is the left child of B and D is the right child of B following the order of the partially order set. The reference data item is C and the data item to be inserted is M. M would first be compared with B, this results in M>B. In addition, M and B would be compared with C which results in M>C and B<C. without using the results of the two last comparisons, the decision logic would indicate to take the next action to move to the right of B in order to use D as the currently traversed data item. This is because M>B. However, using the results of the two last comparisons in accordance with the present disclosure may require to invert that decision logic. Since M>C and B<C are different comparison results, because M is succeeding the reference data item C while B is preceding the reference data item C, the decision logic is to be inverted such that the next action is to move to the left of B and use A as the currently traversed data item.

At the currently data item A, comparing A with the to-be inserted data item M results in M>A. Without using the results of the two following comparisons, the decision logic indicates that the next action is to insert M in the right child node of A. M and A would be compared with C which results in M>C and A<C. Since M>C and A<C are different comparison results, because M is succeeding the reference data item C while A is preceding the reference data item C, the decision logic is to be inverted such that the next action is to move to the left of A for inserting the data item M.

In step 307, the created relation is provided. For example, the tree data structure 320 may be replaced by the second tree data structure and/or the access requests of the tree data structure 320 are redirected to the second tree data structure.

Figure 4:
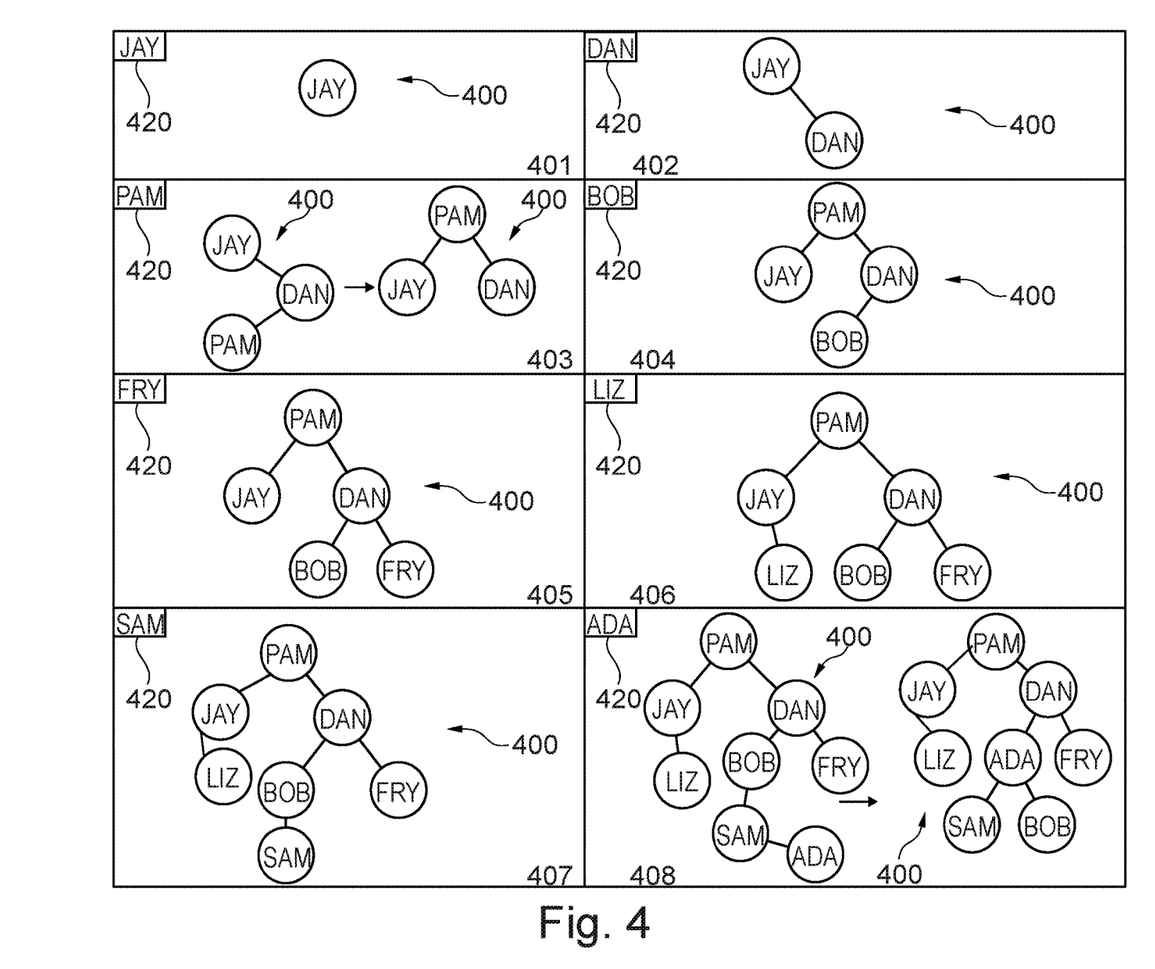
FIG. 4 is a flow diagram of a method for building an example relation in accordance with the present disclosure.

FIG. 4 is a flow diagram of a method for building an example relation in accordance with the present disclosure. The relation to be built may be a rooted tree. The diagram of FIG. 4 includes blocks 401-415 indicating the evolution of the built relation. The built relation is obtained by constructing a tree 400 using a cyclic shift in accordance with the present method.

The tree 400 may be built using the tree 320 of FIG. 3. The tree 320 may be a binary tree containing first names as shown in FIG. 3. According to the tree's characteristic of exposing the items' linear order, "ADA" is the tree's leftmost node and "ZAC" the rightmost node. For the sake of simplicity, the order in which the data items of the tree 320 have been inserted into the second relation 400 is the following: JAY, DAN, PAM, BOB, FRY, LIZ, SAM, ADA, CHE, EVE, HAL, KEN, MIA, RAY, ZAC. This enables to insert in tree 400 data items level by level of the tree 320 e.g. as soon as the data items of a given level (from left to the right) of the tree 320 are inserted in the tree 400, the next level of the tree 320 is used and so on. The order in which the data items are to be inserted is provided for exemplification purpose only. Data items may be inserted in the relation item by item as soon as they are received. This may result in receiving these items in any other order which may cause more imbalances that would cause the tree to rebalance more often.

Each block 401-415 indicates the current status of the tree 400. In every block 401-415, the currently inserted data item 420 is written in the upper left corner and further contains the tree 400 in its current state after insertion of the data item 420. For example, block 402, indicates that data item "DAN" is the currently inserted data item in the tree 400, and the resulting content of the tree 400 is comprised in the block 402. If, for example, at a given block 401-415, the insertion of a data item 420 generates a dysbalance of the tree 400, the rebalancing of the tree 400 is performed and the resulting rebalanced tree 400 is also shown in the given block.

In this example of FIG. 4, the reference data item (also referred to as cyclic shift value e.g. the value at which the domain is split open) is chosen as "IXY". The traversal algorithm 224 may be adjusted as described above with reference to FIG. 3 using the cyclic shift "IXY" as the reference data item.

The adjusted traversal algorithm may be described as follows considering the example of the insertion of a data item "A". Assuming "B" is the currently traversed node of the tree 400 and 'C' is the cyclic shift.

If A<B, the traversal algorithm 224 dictates to go left child node of B. However, two cases raises with the present method:

if A<C and B>C, that behavior is inverted and the adjusted traversal algorithm moves to the right child node of B.

if A<C and B<C, that the adjusted traversal algorithm dictates to go to the left child node of B as the traversal algorithm 224 would dictate.

Following the example of FIG. 4, and taking as an example the block 403. Block 403 indicates the insertion of data item "PAM" in the tree 400 of immediately preceding block 402. For inserting data item "PAM" in the tree 400 of block 402, the tree 400 of block 402 is traversed starting from the root node "JAY". "PAM" is first compared with "IXY" and "JAY" is compare to "IXY". Since "PAM">"IXY" and "JAY">"IXY", the next node to be traversed may be selected like in the traversal algorithm 224 by choosing "DAN" (right child of "JAY") as the next node to be traversed because "PAM">"DAN". Next, "DAN" is compared with "IXY", and since "DAN"<"IXY" and "PAM">"IXY", the adjusted traversal algorithm may select the opposite left node of "DAN" instead of choosing the right node as the traversal algorithm 224 may do because "DAN"<"PAM". The description of block 403 holds true for the remaining blocks of FIG. 4.

In the last block 415 (after inserting data item ZAC), the newly constructed tree 400 contains the former edge nodes ADA and ZAC at unsuspicious locations (they are not even directly connected). New edge nodes are JAY and HAL, according to the chosen reference data item C=IXY. Apart from that, the tree 400 is consistent in itself an can be used for inequality searches just as a tree constructed by the traversal algorithm 224, as long as the C value is taken into account.

The following example describes the adjusted traversal method when used for searching for data item "DAN" in the resulting tree 400 of the last block 415.

A request may be received. The request is for searching a data item of tree 400 having the value "DAN". For that, the tree 400 may be traversed in order to find if the value "DAN" is stored in the tree 400. First, "DAN" may be compared with the root node "PAM". The root node "PAM" is the currently traversed data item. This results in the comparison result indicating that "DAN" is preceding or smaller than "PAM". Following the traversal algorithm 224, this would indicate the next action to traverse the left sub tree of the node containing "PAM" in order to choose the next data item "KEN". However, with the present method the next action may change because two additional comparisons may be performed and their results may influence the next action. The first comparison is between "DAN" and the reference data item "IXY" and the second comparison is between PAM and "IXY". This results in two comparison results namely "PAM>IXY" and "DAN<IXY". The two comparison results are different because PAM is higher than IXY, while the search term DAN is smaller than IXY. Since the two comparison results are different the decision to scan or to traverse the left subtree may be inversed such that the right sub tree of the tree 400 which is to be traversed and the next data item to be chosen is BOB. The currently traversed data item becomes then BOB.

Second, the data item "DAN" may be compared to the currently traversed data item "BOB". This results in the comparison result indicating that "DAN" is succeeding or higher than "BOB". Following the traversal algorithm 224, this would indicate the next action to traverse the right sub tree of the tree having the node BOB as root node in order to choose the next data item "EVE". However, with the present method the next action may change because two additional comparisons may be performed and their results may influence the next action. The first comparison is between "DAN" and the reference data item "IXY" and the second comparison is between "BOB" and "IXY". This results in two comparison results namely "BOB<IXY" and "DAN<IXY". The two comparison results are equal because BOB is smaller than IXY, and the search term DAN is also smaller than IXY. Since the two comparison results are not different the decision to scan or to traverse the right subtree of the node containing "BOB" having the node BOB as the root node may be maintained such that that right sub tree is to be traversed and the next data item to be chosen is EVE.

Third, the data item "DAN" may be compared with the currently traversed data item "EVE". This results in the comparison result indicating that "DAN" is preceding or smaller than "EVE". Following the traversal algorithm 224, this would indicate the next action to traverse the left sub tree of the tree having the node EVE as root node in order to choose the next data item "DAN". However, with the present method the next action may change because two additional comparisons may be performed and their results may influence the next action. The first comparison is between "DAN" and the reference data item "IXY" and the second comparison is between "EVE" and "IXY". This results in two comparison results namely "EVE<IXY" and "DAN<IXY". The two comparison results are the same because EVE is smaller than IXY, and the search term DAN is also smaller than IXY. Since the two comparison results are not different the decision to scan or to traverse the left subtree of the tree having the node EVE as the root node may be maintained such that that left sub tree is to be traversed and the next data item to be chosen is DAN. The currently traversed data item is DAN which is the requested data item which may then be provided as the result of the request. The data item DAN may be associated with referential connections to second data items that the requester may use for data analysis or data access.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures.

For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A method for securing access to a first relation, the first relation comprising data items, the data items forming a partially ordered set in the first relation, wherein an insertion of a data item in the first relation is performed by a traversal method for traversing the first relation until reaching an insert position, the traversal method comprising at a currently traversed data item of the first relation: an order comparing step comprising comparing the data item to be inserted with the currently traversed data item resulting in a current comparison result, and a decision step comprising executing a decision logic for selecting one of a first and second sub-relations of the first relation based on the current comparison result in order to perform a next action, wherein the next action comprises a selection of a next data item to be traversed or to identify the insert position in the selected sub-relation, wherein each of the first and second sub-relations comprises zero or more data items succeeding and preceding the currently traversed data item respectively, the method comprising:

predefining a reference data item;
creating a second relation and inserting a given data item of the first relation into the second relation;

inserting each data item of the first relation into the second relation using the traversal method, wherein the order comparing step comprises in case a comparison result of the currently traversed data item with the reference data item is different from a comparison result of the to be inserted data item with the reference data item inverting the decision logic, and using the inverted decision logic in the decision step;

providing the second relation.

2. The method of claim 1, the method further comprising replacing the first relation with the created relation and/or redirecting data access request of the first relation to the second relation.

3. The method of claim 1, wherein the reference data item is a randomly chosen data item that is part or not part of the first relation.

4. The method of claim 1, the first relation being stored on a server, the server being coupled to a client computer via a network, the client computer storing the reference data item, wherein the created relation is stored on the server.

5. The method of claim 1, wherein the first relation constitutes rooted tree, wherein the given data item is the root node of the first relation, wherein the inserting of each data item of the first relation comprises traversing the first relation and inserting data items of each level of the first relation before moving to the next level of the first relation.

6. The method of claim 1, the first relation being stored on a server, the server being coupled to a client computer via a network, wherein the inserting of a data item of the first relation in the second relation is comprising: requesting by the client computer the data item to be inserted from the server and receiving the requested data item, performing by the client the traversal method, the client further instructing the server for performing the inserting steps.

7. The method of claim 6, wherein the data items of the first relation are encrypted data items, the receiving of the requested data item comprising decrypting the requested data item.

8. The method of claim 6, wherein the inserting of the data item comprises re-encrypting the received data item and sending the encrypted data item to the server in order to be inserted in accordance with the determined next action.

9. The method of claim 1, wherein the second relation comprises a rooted tree, wherein after each inserting step the method comprises rebalancing the created relation in response to determining that the resulting second relation from the inserting step is imbalanced.

10. The method of claim 1, wherein the partially ordered set comprises data items forming a rooted binary tree, wherein the insert position is a leaf node.

11. The method of claim 1, the partially ordered set comprising an AVL tree.

12. The method of claim 1, further comprising encrypting the second relation.

13. The method of claim 1, the method further comprising receiving a request for performing one of an inequality search, interval search and prefix search on the second relation, and traversing the second relation using the adjusted traversal method in order to execute the request.

14. The method of claim 1, further comprising replacing the first relation with the second relation in the server and/or redirecting data access request of the first relation to the second relation.

15. The method of claim 1, further comprising: determining two other reference data items, and for each sub-relation of two sub-relations of the second relation comprising data items succeeding and preceding the given data item respectively, repeating the inserting steps using the sub-relation as the first relation.

16. A computer program product comprising computer executable instructions to perform the method as claimed in claim 1.

17. A client system comprising a processor and a memory, the memory comprising instructions that wherein the execution of the instructions cause the processor to perform the method of claim 1.

* * * * *